United States Patent [19]
Sitte et al.

[11] Patent Number: 5,438,838
[45] Date of Patent: Aug. 8, 1995

[54] CHAMBER FOR FREEZE-DRYING BY CRYOSORPTION

[75] Inventors: Hellmuth Sitte, Seefeld in Tirol, Austria; Klaus Neumann, Bexbach-Saar, Germany; Ludwig Edelmann, Homburg-Saar, Germany; Helmut Haessig, Homburg-Saar, Germany; Heinrich Kleber, Wien/Strebersdorf, Austria

[73] Assignee: Leica AG, Wien, Austria

[21] Appl. No.: 232,151

[22] PCT Filed: Sep. 6, 1993

[86] PCT No.: PCT/EP93/02409
§ 371 Date: Jun. 1, 1994
§ 102(e) Date: Jun. 1, 1994

[87] PCT Pub. No.: WO94/05996
PCT Pub. Date: Mar. 17, 1994

[30] Foreign Application Priority Data
Sep. 8, 1992 [AT] Austria .................. 1788/92

[51] Int. Cl.⁶ ............... F25D 3/10; F04B 37/08; F26B 5/06
[52] U.S. Cl. ................. 62/55.5; 62/51.1; 62/78; 34/92; 34/294
[58] Field of Search ............... 62/51.1, 55.5, 78; 34/92, 294

[56] References Cited

U.S. PATENT DOCUMENTS

| | | | |
|---|---|---|---|
| 2,465,229 | 3/1949 | Hipple, Jr. | 62/55.5 X |
| 3,009,258 | 11/1961 | Taylor | 34/92 |
| 3,216,207 | 11/1965 | Boyer et al. | 62/55.5 X |
| 3,309,844 | 3/1967 | Hemstreet et al. | 62/55.5 X |
| 3,330,125 | 7/1967 | Klipping | 62/55.5 |
| 3,668,881 | 6/1972 | Thibault et al. | 62/55.5 |
| 4,232,453 | 11/1980 | 34 | 92/ |
| 4,306,425 | 12/1981 | Sitte et al. | 62/51.1 |
| 4,799,361 | 1/1989 | Linner | 34/294 X |
| 4,976,111 | 12/1990 | Larin | 62/55.5 |
| 5,014,517 | 5/1991 | Larin et al. | 62/55.5 |

FOREIGN PATENT DOCUMENTS

2739796 3/1979 Germany.

OTHER PUBLICATIONS

Coulter et al., "Preparation of Biological Tissues for Electron Microscopy by Freeze-drying", 1960, pp. 477–494.

Ingram et al., "Freeze-Dried, Plastic-Embedded Tissue Preparation: A Review", Scanning Electron Microscopy, IV, 1980, pp. 147–160.

(List continued on next page.)

Primary Examiner—Christopher Kilner
Attorney, Agent, or Firm—Foley & Lardner

[57] ABSTRACT

A chamber system for cryosorption freeze-drying of biological specimens in a Dewar vessel, comprises a chamber having a cylindrical metal wall and fitted within the Dewar vessel, a lower outer edge of which chamber is connected in a vacuum-tight manner to a lower edge of a metallic rotational component, the metallic rotational component having a bottom contact surface, which bottom contact surface corresponds with a complementary top contact surface on top of a cylindrical body around which liquid nitrogen flows and cools the metallic rotational component, the rotational component having a chamber to receive a drying agent for conducting cryosorption, for example a molecular screen, as well as a connection to the drying chamber.

The upper edge of the metal wall or a ring connected thereto in a vacuum-tight manner is situated outside the Dewar vessel and is therefore approximately at ambient temperature and has a vacuum connection for the connection of commercially available vacuum components. The opening at the top of the ring is preferably sealable in a vacuum-tight manner by a commercially available O-ring in conjunction with a cover.

20 Claims, 2 Drawing Sheets

OTHER PUBLICATIONS

Linner et al., "Cryopreparation of Tissue for Electron Microscopy", 1986, pp. 1123–1135.

J. G. Mellor, "Fundamentals of Freeze–Drying", Academic Press, 1978.

H. T. Meryman, "Cryobiology", Academic Press, 1966, pp. 609–663.

K. Neumann, "Grundrisse der Gefriertroknung", Musterschmidt–Verlag, Goettingen, 1952.

L. Edelmann, "Freeze–Drying of chemically Unfixed Biological Material for Electron Microscopy", Mikroskopie, Vienna, 1979, 35, 31–36.

L. Edelmann, "Freeze–Dried Embedded Specimens for Biological Microanalysis", Scanning Electron Microscopy, 1986, 1337–1356.

Carlemalm et al., "Low Temperature Embedding", Science of Biological Specimen Preparation, 1986, pp. 147–154.

CHAMBER FOR FREEZE-DRYING BY CRYOSORPTION

BACKGROUND OF THE INVENTION

1. Field Of the Invention

The present invention relates to a chamber for freeze-drying by cryosorption, wherein cooling is effected by liquid nitrogen in a Dewar vessel.

2. Description of Related Art

In order to better present fine structures or features of a biological specimen under an optical or electron microscope, especially in the case of histochemical applications, freeze-drying (hereinafter referred to as "FD") of a biological specimen is becoming more widely used. Typically, when a biological specimen is freeze-dried, the specimens are, without any pretreatment, frozen extremely rapidly ("cryofixation") and subsequently dried, preferably in a vacuum at temperatures of around −80° C. (in this connection, c.f. inter alia H. D. Coulter and L. Terracio, Anat. Rec. 187, 477–494, 1960; V. Hanzon and L. H. Hermodsson, Ultrastruct. Res. 4, 332–348, 1960; F. D. Ingram and M. J. Ingram, Scanning Electron Microscopoy, IV, 147–160, 1980; J. G. Linner et al., J. Histochem. Cytochem. 34, 1123–1135, 1986; J. D. Mellor, Fundamentals of Freeze-Drying, Academic Press, London, 1978; H. T. Meryman in H. T. Meryman, Editor, Cryobiology, Academic Press, Sn. 609–663, 1966; K. Neumann, Grundriβ der Gefriertrocknung (Outline of Freeze Drying), Musterschmidt Verlag, Göttingen, 1952; and references and publications cited therein).

According to the cited prior art, in most instances, freeze-drying of biological specimens is conducted in systems wherein the vacuum is generated by a two-stage pump system (a rotary prevacuum pump with a diffusion high vacuum pump) or a single stage pump system (a turbomolecular pump), and the external cooling of the biological specimens and condensation surfaces is carried out with liquid nitrogen (hereinafter referred to as "LN$_2$"). In addition to the considerable expense of the apparatus and equipment necessary to conduct the freeze-drying of biological specimens in this manner, very high operating costs are also incurred because the majority of commercially available or laboratory systems use over 1 liter of LN$_2$ per hour and also because even FD of small specimens having a diameter of less than about 1 mm requires an average of approximately 14 days. Moreover, a majority of these systems generate high levels of noise owing to the continuously running rotary pumps and therefore does not permit operation of such FD systems in common areas. Another drawback of these systems stems from the especially high labor costs associated with the need to continuously and frequently refill the LN$_2$. Attempts at automating the chore of refilling LN$_2$ have the effect of increasing the capital expenditure to a considerable extent.

Finally, a substantial additional disadvantage of these systems resides in the fact that all rotary pumps and diffusion pumps liberate oil vapors, which are deposited on the cold object surfaces and, as a result of this, alter such surfaces artifactually.

Accordingly, repeated attempts were made to use cryosorption systems for the generation of a clean oil-free high vacuum (in this connection, c.f., inter alia German Patent DE 27 39 796 as well as L. Edelmann, Microscopy, Vienna, 35, 31–36, 1979; L. Edelmann, Scanning Electron Microscopy, IV, 1377–1356, 1986; and further literature references cited therein). The system developed and used by Edelmann comprises a divisible cylindrical container with a volume of approximately 0.5 liter, which is connected in a vacuum-tight manner to a tube, the free end of which is equipped with a valve and a hose connection. In the lower part of the container there is a molecular screen as a drying agent. A thermostatically heatable tray to receive the frozen specimens is secured in the upper part of the container. After filling of the molecular screen and loading of the specimen tray with the frozen specimens, both parts are screwed to one another in a vacuum-tight manner. Thereafter, the container is introduced into an LN$_2$-filled Dewar vessel. At this point, all of the wall surfaces of the container are in direct contact with LN$_2$ (temperature −196° C.), and the molecular screen is also cooled and adsorbs most of the gas molecules (O2, N$_2$, CO$_2$, H$_2$O) present in the container. Depending upon whether and to what extent the noble gases are or are not drawn off by a prevacuum pump, the result is a vacuum between $10^{-3}$ and $10^{-5}$ torr, which is entirely sufficient for an efficient FD, relative to the given mean free path length of the H$_2$O molecules. The situation is additionally improved in that H$_2$O is permanently deposited on the chamber walls directly cooled by LN$_2$, and in that the decisive water vapor partial pressure of this arrangement becomes almost immeasurably small as a result of this. A particular advantage of the described arrangement finally resides in that the LN$_2$ consumption of the system is below 1 liter of LN$_2$ per day. Accordingly, drying over 14 days in a 35 liter Dewar vessel can be performed without LN$_2$ refilling and without noise.

As against the cited advantages of cryosorption FD according to Edelmann, there are disadvantages which oppose its routine use. These include in the first instance the complicated loading of the chamber with the molecular screen and the frozen specimens. At low temperatures and when the container is in the first instance open, the molecular screen immediately absorbs gases and this leads to a loss of cryosorption capacity. The sealing of the two-part chamber is very difficult and requires high forces, since only hard sealing rings, preferably metal seals, are suitable in the temperature range <−180° C. It is very difficult to secure the correct position of the specimens in the hollows of the specimen tray during this procedure. Finally, any visual monitoring and UV polymerization in this system is impossible. All cited problems are likewise applicable, in some cases to an intensified extent, to the removal of the specimens which have become extremely hygroscopic as a result of the FD.

In view of the indisputable advantages of a cryosorption system for FD, an object of the present invention is to provide an arrangement which fully exploits the advantages of the Edelmann container without its disadvantages, and is thus competent for routine use without restrictions.

According to the present invention, this object is achieved as a refinement or improvement of the Edelmann concept by providing a chamber for freeze-drying by cryosorption, having a cooling effected by liquid nitrogen, which chamber is situated in a Dewar vessel and cools a body having good thermal conductivity, wherein the chamber comprises a cylindrical metal outer walling and is primarily situated within the Dewar vessel, preferably within the neck of the Dewar vessel, the lower edge of the cylindrical metal outer walling of the container being connected in a vacuum-tight manner to a lower edge of a rotary component which is preferably rotationally symmetric, the rotary component having a planar bottom exhibiting a contact surface, which planar bottom corresponds with the likewise preferably planar complementary surface on top of a cylindrical body around which liquid nitrogen flows and which is cooled by this cylindrical body, the rotary component having a chamber for receiving the drying agent for cryosorption, for example a molecular screen, as well as a connection to the drying chamber, an upper edge of the cylindrical metal walling optionally having a ring which is connected thereto in a vacuum-tight manner situated outside the Dewar vessel and therefore approximately at ambient temperature. To this end, the arrangement according to the invention exhibits a cooling which takes place in a known manner on the floor surface of a container, such that this floor surface corresponds with a complementarily designed surface on the top of a $LN_2$-cooled solid body which is situated in a Dewar vessel, and the height of the $LN_2$ level in the Dewar vessel does not exert any significant influence on the temperature of the contact surface because of the material cross section and of the thermal conductivity of this solid body, which temperature as a rule differs from the $LN_2$ temperature ($-196°$ C.) by at most 20° C.

The floor of the FD chamber is preferably a part of a rotary component of a metal of good thermal conductivity (e.g., brass or aluminum), which exhibits a chamber to receive a drying agent (e.g., "zeolite" molecular screen) as well as, at its top, a depression for a tray for receiving the frozen specimens. The chamber for the drying agent exhibits at least one connection to the freeze-drying chamber and, if required, in addition an opening, which opening can be sealed in a vacuum-tight manner, for the filling and exchange of the drying agent. The side walls of the chamber are formed by a preferably cylindrical sleeve of a thinmetal sheet of poor thermal conductivity (e.g., fine steel sheet in a thickness of approximately 0.2 to 1 mm and a height > 100 mm). The cylindrical sleeve is connected at its lower end in a vacuum-tight manner to the aforementioned rotary component, and at its upper edge, likewise in a vacuum-tight manner, to a metal ring having good thermal conductivity. The position of the chamber and the height of the side walls are dimensioned so that at least the topmost portion of the chamber with the metal sealing ring projects from the neck of the Dewar vessel.

Accordingly, under normal operating conditions during FD, the topmost portion of the chamber is at a temperature which is above the dew point of normal ambient air. In this way, it is possible to seal off the sealing cover, over the opening in the upper sealing ring of the chamber, with a commercially available O-ring. Identical conditions apply to a normal vacuum connection (e.g., standard flange), which can preferably be disposed in that region of the chamber which projects out of the Dewar vessel, for example again at the upper sealing ring, and connects the FD chamber space to the ambient air. It is possible to connect to it any commercially available vacuum components (e.g., vacuum meter, valves, hose connections for prevacuum pumps, etc.).

To receive and thermostatically heat the frozen specimens, it is possible to provide a tray in the depression at the top of the floor rotary component of the chamber, which tray exhibits a heating cartridge and a temperature sensor for the thermostatic heating as well as, at its top, at least one hollow to receive the frozen specimens. The mounting of this tray on the floor rotary component takes place preferably by point or line overlays, in such a manner that only a minimal amount of thermal contact results between the deep-frozen rotary component ($< -176°$ C.) and the specimen tray, which tray is normally heated to approximately $-80°$ C. for FD.

An additional feature of the present invention resides in the floor rotary component upon which additional cooling surfaces may be attached and thereby increase the binding of $H_2O$. For the permanent assurance of a thermal contact, that cannot be influenced by manipulation forces, between the floor surface of the chamber and the complementary solid body surface in the Dewar vessel, the chamber may be screwed together with the Dewar vessel or to a mounting component fastened to the Dewar vessel. Moreover, according to the present invention, a screw connection component which is pretensioned by spring elements can compensate for any length changes of the cooled parts.

A further feature of the present invention is that valves effect a blocking of the chamber with the drying agent in the floor component, as well as an opening of a connection to the interior of the Dewar vessel and thus a flooding of the FD chamber with dry cold nitrogen gas (hereinafter referred to as "$GN_2$"). The first valve, can at the same time, be designed as an overpressure valve and thus protect the user against a spontaneous release of adsorbed gases when after lengthy dry periods and as the chamber warms up after vaporization of the last $LN_2$ residues from the Dewar vessel, the absence of special precautions could lead to an explosion of the floor part.

A further feature of the present invention is that additional vacuum connections, as well as a further valve with a downstream hose connection for the preevacuation of the chamber space for the removal of a major part of the noble gases are provided. Moreover, the cover for sealing the upper chamber opening may comprise a transparent and/or UV-transmitting material. Further, the upper sealing ring and the valves are provided with at least one heating cartridge and a temperature sensor, which permit a thermostatic heating of these elements as protection against a disturbing cooling during a relatively long period of flooding of the chamber with dry cold $GN_2$.

Further advantages and features of the invention will be evident from the description, which follows, of preferred exemplary embodiments with reference to the drawings.

Figure 1A:
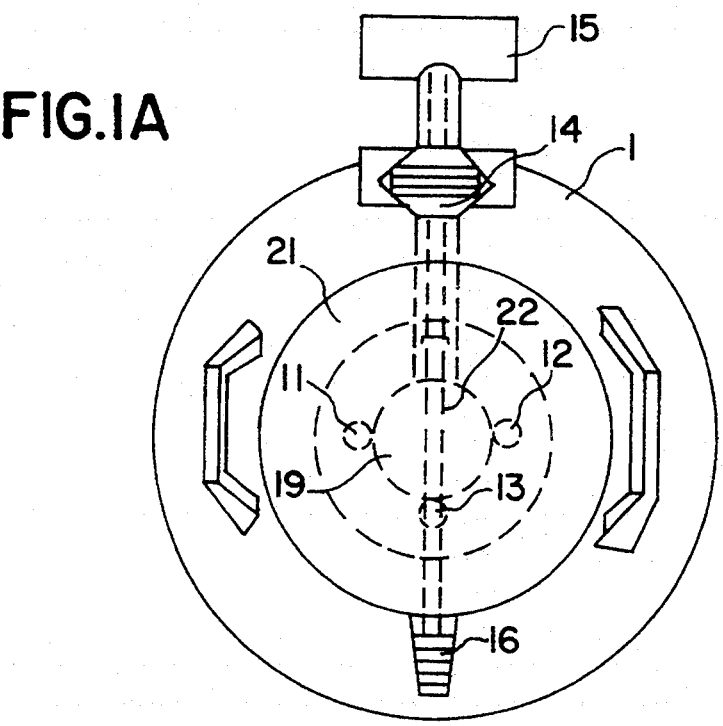
FIG. 1a is a diagrammatic plan view of the chamber arrangement of the present invention.
Figure 1B:
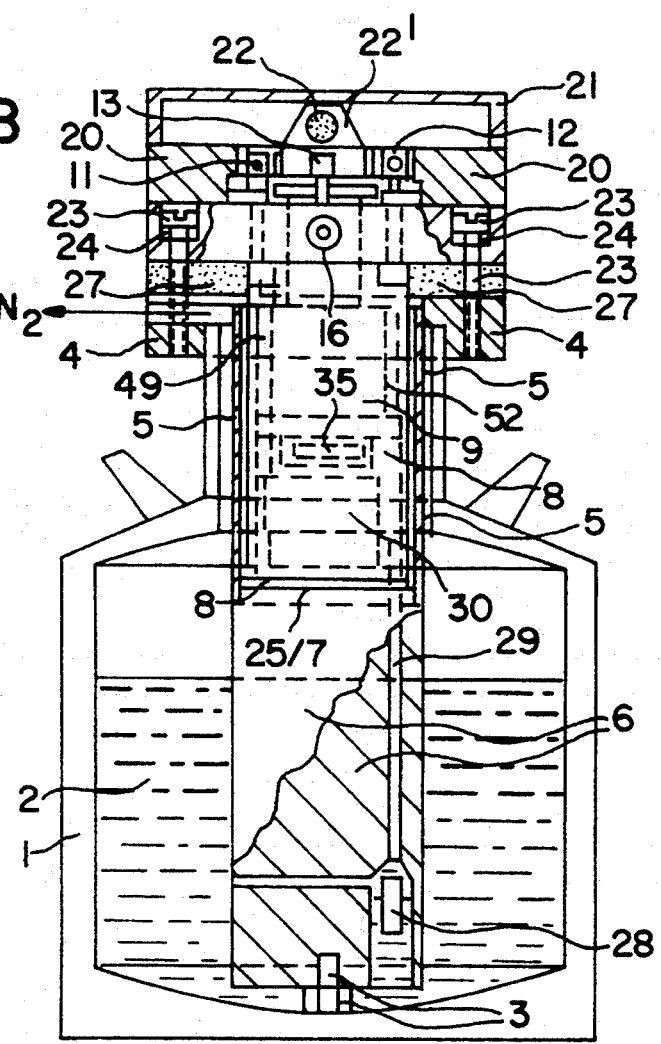
FIG. 1b is a diagrammatic, partial cross-sectional view thereof; showing the Dewar vessel with the stationary insert and the FD chamber set thereon, inclusive of a further attachment with a UV radiator for UV polymerization embedding in the chamber.

The chamber, according to the present invention, for FD by cryosorption as shown in FIGS. 1a and 1b, is inserted, in accordance with the prior art, into a Dewar vessel 1 with a filling of $LN_2$ 2, which vessel contains an insert 6, for example an aluminum cylinder 6 (material cross section $>10$ cm$^2$), which is supported on a bolt 3 on the Dewar floor, as well as on the sealing ring 4 of the vessel 1 via a sleeve 5 of thin-walled fine steel sheet. The upper boundary surface 7, which is preferably planar, exhibits to a large extent independently of the $LN_2$ filling level, a permanent temperature differential of about 20° C. (maximum) with the temperature of $LN_2$ ($-196°$ C.). The FD chamber according to the present invention preferably comprises a rotary component 8 having a floor surface 25 which floor surface 25 complementarily corresponds with the surface 7 of the metal body 6 and exhibits a temperature below $-176°$ C. as a result of good thermal contact when the $LN_2$ filling of the vessel 1 is carried out. At its lower edge, the rotary part 8 is connected in a vacuum-tight manner to a preferably cylindrical sleeve 9 made of a thin metal sheet of low thermal conductivity (e.g., fine steel sheet having a thickness of 0.2 to 1 mm and a height $>100$ mm).

The upper edge of the cylindrical sleeve 9 projects from the neck of the Dewar vessel 1 and is connected, preferably in a vacuum-tight manner, to a ring 10 made of a metal having good thermal conductivity. Preferably, there can be disposed on this ring 10 valves with operating knobs 11, 12 and 13, as well as a vacuum connection, for example, a standard flange 14, for the connection of a gauge tube 15 for vacuum measurement or other commercially available vacuum components and/or a hose connection for the pre-evacuation of the FD chamber. The opening of the ring 10 can be sealed in a vacuum-tight manner by a cover 19 and an O-ring 18.

Onto the ring 10 there can be set for example via the intermediate element 20, a housing 21 for the UV radiator 22 with reflector 22' which permits in the chamber a UV polymerization (in this connection, c.f., E. Carlemalm et al., in M. Müller et al., Editors, The Science of Biological Specimen Preparation, IV, 147 et seq., SEM Inc. Chicago, 1986; and further literature cited therein). The chambers 8, 9, 10, 18, 19 may be secured for security against the manipulation forces that are typical during operation as well as against tilting by an additional connection such as, for example, a screw connection means such as stay bolts 23, which are anchored in the sealing ring 4 at the neck of the Dewar vessel 1 and, if required, are maintained by a spring (e.g., cup springs 24), and the spring force locks the contact of the corresponding surfaces 7/25 and thus locks the required thermal contact, even in those circumstances in which the lengths of various components vary due to temperature fluctuations.

To the extent that the $GN_2$ escaping from the $LN_2$ 2 in the Dewar vessel 1 escapes exclusively or predominantly through an opening, for example through the channel 25 in the mounting ring 4 at the neck of the Dewar vessel 1, a sealing ring 27 of flexible material (e.g., Moltopren) can prevent the entry of damp ambient air, and thus frost formation in the neck of the Dewar vessel 1 is prevented. According to the prior art, a flooding of the FD chamber with dry cold $GN_2$ can be effected in the shown manner (c.f., FIGS. 1a, 1b and 2) in that a heating cartridge 28 vaporizes and releases $GN_2$ from the $LN_2$, into a bore 29 of the cylinder 6, which bore 29 communicates with a bore or a tube 52, which extends for example through the rotary component 8.

Figure 2:
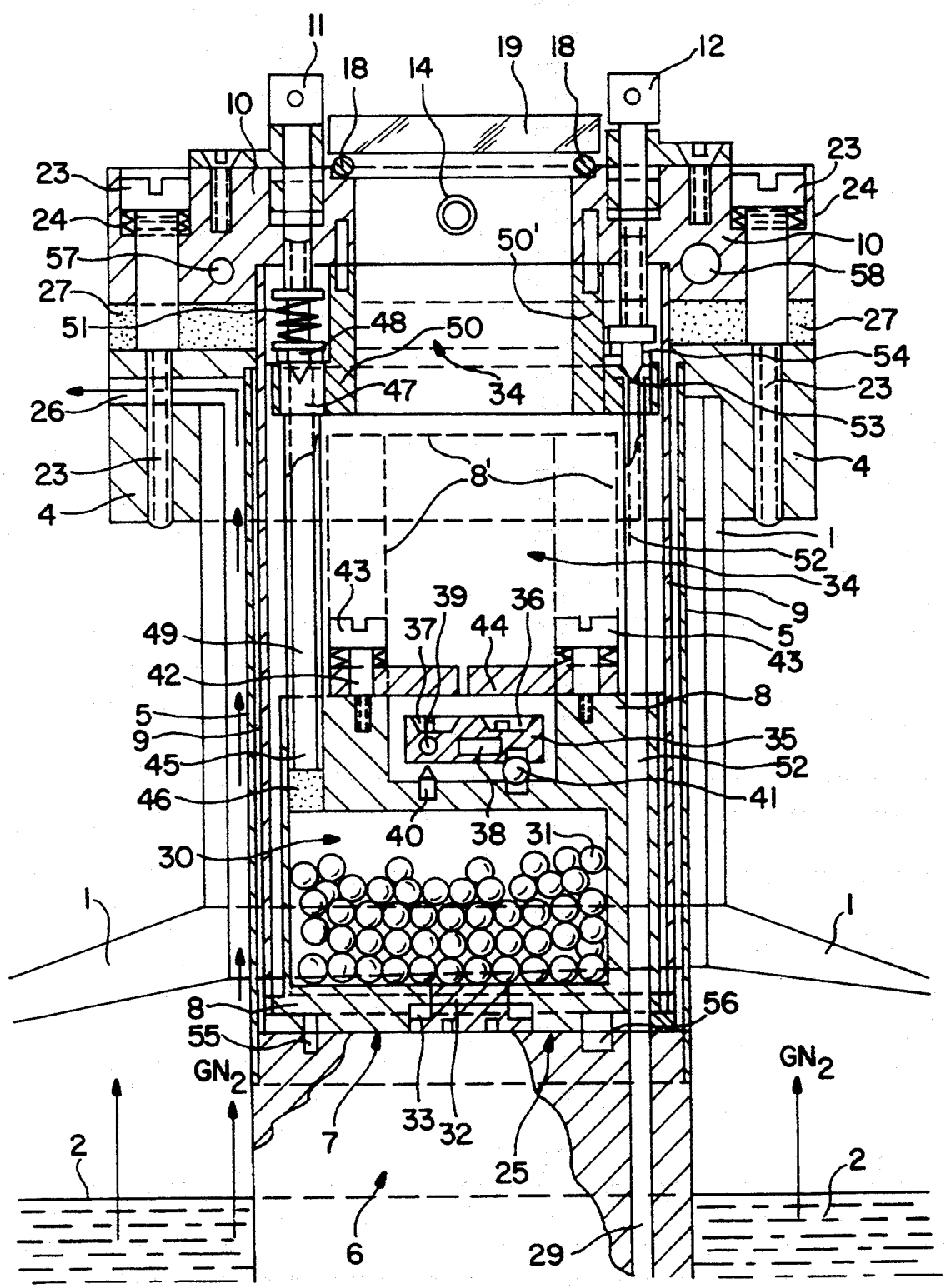
FIG. 2 is another diagrammatic, partial cross-sectional view thereof.

The detailed design of the FD chamber according to the present invention is evident from the representation in FIG. 2. The rotary component 8 exhibits a chamber 30 to receive a drying agent 31 (e.g., molecular screen), which can be exchanged, for example, after opening a cover 32. A seal (e.g., copper ring 33) assures a permanent vacuum-tight connection, even at temperatures below $-180°$ C. At the floor of the drying chamber 34 formed by the surface of components 8, 9, 10, 18, 19, there is situated in a depression of the rotary component 8 a tray 35 with at least one hollow 36 to receive frozen specimens 37. The tray 35 can be thermostatically heated by means of a heating cartridge 38 and a temperature sensor 39 and is connected to the walling of the rotary part 8 merely via point contacts (e.g., tip overlays 40) or line contacts (e.g., spheres 41 made of material having poor thermal conductivity, e.g., glass, which rest in corresponding overlay bores in the components 8 and 35 respectively). Relatively large heat transfers between elements 8 and 35 are avoided in this way during vacuum operation.

A further feature of the present invention is that for the expansion of the cold surfaces of the rotary component 8, additional condensation surfaces for water vapor are provided by elements 44 that are articulated in a resilient manner (e.g., cup springs 42) via stay bolts 43. The contact surfaces of the corresponding parts 8 and 44 are, for example, designed to be precisely planar having regard to a perfect thermal contact and, if required, are covered with a thermally conductive liquid or paste of low vapor pressure. Upon insertion and upon removal of the specimens 37, the condensation elements 44 can either be laterally pivoted away or entirely removed after removal of the stay bolts 43.

A further feature of the present invention is that the connection 45 may be provided with a network or filter 46 for protection against entry of dust particles (e.g., abrasion from the molecular screen 31) from the chamber 30 into the chamber 34 and, further, can be sealed off by a valve 47/48. The valve seating 47 can be secured on, for example, a thin-walled fine steel tube 49 connected in a vacuum-tight manner to the rotary component 8, and can also be surrounded by a metal component 50, which has good thermal conductivity and which is in good thermal contact with the upper sealing ring 10. The valve 47/48 is opened or closed by rotation of the knob 11 and at the same time serves by way of the spring (e.g., helical spring 51) in a technically known manner the function of an overpressure valve, which overpressure valve resiliently opens in the limiting position of the knob 11, when an overpressure condition arises in the chamber 30.

Still another feature of the present invention is that there are provided in the ring 10 in a technically known manner a shut-off valve (operating knob 13 in FIG. 1) with a downstream hose connection 16 (FIG. 1) for connection to a water jet pump or membrane pump, which ensures against the risk that oil deposits form on the frozen objects. Moreover, a fine steel tube 52 connected in a vacuum-tight manner to the rotary component 8 may be connected in a vacuum-tight manner to a further valve 53/54, which valve 53/54 may be opened and closed using knob 12. The valve seating 53 that corresponds to the valve seating 47 is thermally coupled by an element 50' to the upper sealing ring 10 of the chamber, and the valve function of this valve, apart from the overpressure security which is not required in this case, corresponds to that of the valve 11/47/48/50. The valve 12/53/54/50' permits the chamber space 34 after conclusion of the FD of the specimens 37 to be flooded with dry cold $GN_2$ from the interior of the Dewar vessel in a manner evident from FIG. 1 and as already described; in this case, orientation aids (e.g., bolts 55/56) assure the required agreement of the spatial positions of the communicating tubes 29 and 52.

A still further feature of the present invention is that the upper sealing ring 10 may be thermostatically heated by means of a heating cartridge 58 and a temperature sensor 57, such that in the case of a relatively lengthy flooding of the drying chamber 34 with cold $GN_2$ from the Dewar interior, neither the valve seatings 47/53 nor the upper sealing ring 10 is cooled in a manner which is disturbing and obstructive to further operation.

In a mutatis mutendis modification or combination of the above described designs, features and refinements, the FD chamber according to the present invention may be designed in very widely differing ways without thereby diminishing its inventive character. Thus, the manner of cooling of the floor surface 25 of the rotary component 8 is without relevance so long as this floor surface is cooled to a temperature which, after the pre-evacuation according to the invention by a drying agent 31, permits in a chamber 30 the achievement or reaching of a vacuum better than $10^{-3}$ torr, as is required for FD. Likewise, it is without relevance where or in what manner an opening is provided for the filling or removal of the drying agent 31 in the chamber 30. The same applies to the design, operation and arrangement of the valves 47/48, and 53/54, which for example may also be disposed directly on the rotary component 8, or their axes rotated 90° and moved horizontally in the ring 10, instead of being moved vertically in the manner as shown in FIG. 2, so that the additional thermal connection to the upper sealing ring may be eliminated. It is immaterial in what way or manner, if and as required, the surface area of the cold components is increased for water binding. An alternative to the described additional cooling elements 44 consists, for example, in the drawing up, indicated in broken lines in FIG. 2, of the edge 8' of the rotary component 8. Further, it is immaterial in what way or manner a perfect contact is assured between the corresponding surfaces 7 and 25 of the rotary component 8 and cylinder 6. For example, screwing 23/24 together of the two components can be replaced by a corresponding orientation by means of a guide element for the FD chamber or by a clamping strap.

We claim:

1. A chamber for freeze-drying by cryosorption with liquid nitrogen, which chamber is situated in a Dewar vessel and cools a body of good thermal conductivity, wherein the chamber comprises:

a cylindrical metal outer walling primarily situated within the neck of the Dewar vessel the lower edge of the cylindrical metal outer walling of the chamber being connected in a vacuum-tight manner to a lower edge of a rotationally symmetric rotary component, the rotationally symmetric rotary component having a planar bottom having a contact surface, which planar bottom corresponds with a complementary planar surface on top of a cylindrical body around which liquid nitrogen flows and is cooled by this cylindrical body, the rotary component having a chamber for receiving the drying agent for cryosorption and a connection to a drying chamber and an upper edge of the cylindrical metal outer walling having a ring connected thereto in a vacuum-tight manner and being situated outside the Dewar vessel at ambient temperature.

2. A chamber according to claim 1, wherein the cylindrical metal outer walling comprises a thin metal sheet having a thickness between about 0.2 mm to 1 mm.

3. A chamber according to claim 2, wherein the metal sheet is a steel sheet.

4. A chamber according to claim 1, wherein the height of the outer walling is at least 100 mm.

5. A chamber according to claim 1, wherein the rotary component has an opening for refilling or exchanging the drying agent and that is sealable in a vacuum-tight manner by a cover with a metal ring seal.

6. A chamber according to claim 1, wherein the ring has at least one vacuum connection and the opening at a top portion of the ring is sealable With an O-ring in conjunction with a cover in a vacuum-tight manner.

7. A chamber according to claim 1, further comprising a metal tray having good thermal conductivity, the tray being thermostatically heatable by means of a heating cartridge and a temperature sensor, the tray further having at its top at least one hollow and connected to the rotary component in a manner such that a high thermal resistance results between the tray and the rotary component when the chamber is evacuated.

8. A chamber according to claim 7, wherein the the rotary component and the tray are connected by means of tip overlays.

9. A chamber according to claim 7, wherein the the rotary component and the tray are connected by means of spheres of low thermal conductivity having a line contact with edges of receiving bores in both the rotary component and the tray.

10. A chamber according to claim 1, wherein at a top portion of the rotary component, there are securable metal components of good thermal conductivity and at least one planar contact surface, the planar contact surface having a good thermal contact with the rotary component, the securable metal components being for the insertion or for the removal of specimens from a tray.

11. A chamber according to claim 1, wherein the chamber is securable by securing securing elements to the Dewar or to a mounting element fixedly connected to the Dewar such that a force locking contact is assured between the corresponding surfaces on the rotary component and the cylindrical body.

12. A chamber according to claim 1, wherein the drying chamber and the chamber for receiving the drying agent are connectable to one another or respectively separable from one another from outside by means of a valve.

13. A chamber according to claim 12, wherein the valve is situated in an upper half of the chamber, and a thin-walled tube of a material of low thermal conductivity is situated between a valve seating and a top of the rotary component adjoining a connecting channel, the material of the thin-walled tube having a wall thickness of less than 0.5 mm, the valve seating being thermally connected to the ring by a metal component of good thermal conductivity.

14. A chamber according to claim 12, wherein the valve is constructed by a spring element as an overpressure valve, which automatically opens in the event of an overpressure in the chamber containing the drying agent.

15. A chamber according to claim 1, wherein the chamber has a valve that connects the drying chamber to the interior of the Dewar vessel with a pipe.

16. A chamber according to claim 15, wherein a portion of the pipe that extends into the chamber comprises a thin walled tube of low thermal conductivity having a wall thickness of less than 0.5 mm, which is connected in vacuumtight manner to the rotary component, and the valve seating is thermally connected to the ring of the chamber by a metal component of good thermal conductivity.

17. A chamber according to claim 1, further comprising a transparent sealing cover.

18. A chamber according to claim 1, further comprising a sealing cover that exhibits a high transparency for UV rays.

19. A chamber according to claim 1, wherein a UV radiator is fitted onto the upper sealing ring.

20. A chamber according to claim 1, wherein the ring of the chamber is thermostatically heatable by means of a heating cartridge and a temperature sensor.

* * * * *